:::

United States Patent [19]

Afriat et al.

[11] Patent Number: 5,573,768

[45] Date of Patent: Nov. 12, 1996

[54] COSMETIC COMPOSITION IN THE FORM OF AN AQUEOUS GEL

[75] Inventors: Isabelle Afriat, Paris; Pierre Fodor, Garches; Francoise Pouget, Fontenay-Sous-Bois, all of France

[73] Assignee: L'Oreal, Paris, France

[21] Appl. No.: 236,138

[22] Filed: May 2, 1994

[30] Foreign Application Priority Data

May 3, 1993 [FR] France .................. 93 05238

[51] Int. Cl.$^6$ .................................... A61K 7/48
[52] U.S. Cl. .............. 424/401; 424/78.02; 424/78.05; 514/844; 514/944
[58] Field of Search .................. 424/401, 78.02, 424/78.03; 514/844–848, 944

[56] References Cited

U.S. PATENT DOCUMENTS

| | | | |
|---|---|---|---|
| 4,629,623 | 12/1986 | Balazs et al. | 424/78 |
| 4,863,725 | 9/1989 | Deckner et al. | 424/81 |
| 5,073,372 | 12/1991 | Turner et al. | 424/401 |
| 5,204,104 | 4/1993 | Bolinger et al. | 424/401 |

FOREIGN PATENT DOCUMENTS

| | | |
|---|---|---|
| 0332501 | 9/1989 | European Pat. Off. . |
| 9219216 | 11/1992 | WIPO . |
| 9301797 | 2/1993 | WIPO . |

OTHER PUBLICATIONS

CIFA "Cosmetic Ingredient dictional" p. 203, 3rd edition (1982).

Primary Examiner—Jyothsna Venkat
Attorney, Agent, or Firm—Cushman Darby & Cushman, L.L.P.

[57] ABSTRACT

Cosmetic composition in the form of an aqueous gel containing a gelling agent and an aqueous medium, in which the gelling agent consists of a mixture of:

a) at least one at least partially neutralized, crosslinked acrylic acid polymer having a molecular weight of between 700,000 and 4,500,000 approximately, b) at least one at least partially neutralized copolymer of acrylic acid and vinyl monomer bearing amine, amidine and nitrile functions, and obtained by hydrolysis of polyacrylonitrile, having a molecular weight of between 100,000 and 200,000 approximately, and c) at least one polyethylene glycol having a molecular weight of between $10^5$ and $3\times10^7$ approximately.

8 Claims, 1 Drawing Sheet

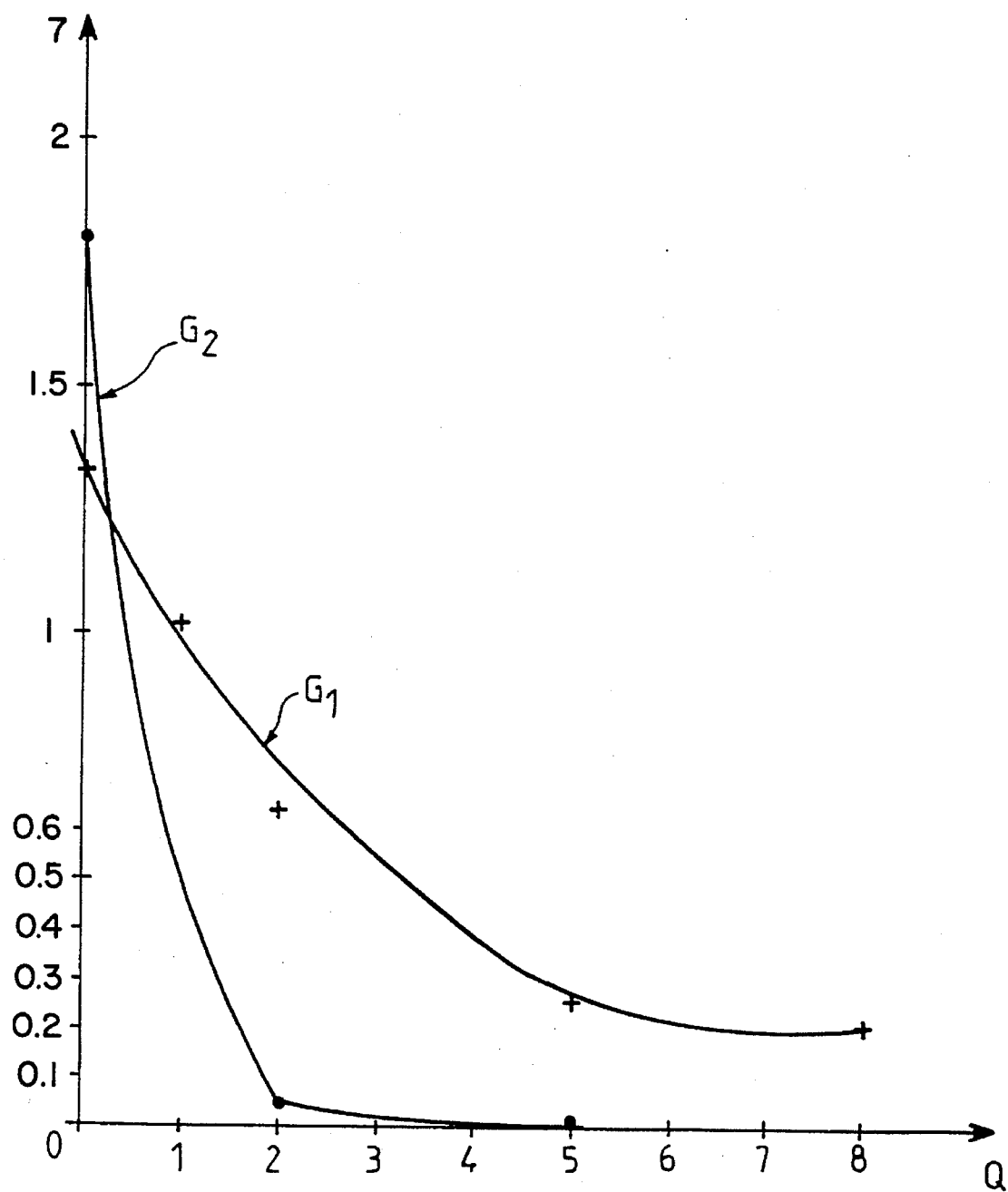

COSMETIC COMPOSITION IN THE FORM OF AN AQUEOUS GEL

The present invention relates to a cosmetic composition in the form of an aqueous gel.

BACKGROUND OF THE INVENTION

Cosmetic compositions for care of the skin were hitherto generally formulated in the form of a cream or milk containing oil as a lubricant ingredient, the presence of oil avoiding drying of the skin and imparting softness to the latter. However, these oil-based formulations have a greasy feel and are often tacky, which is unpleasant for the user and annoying to the latter.

To avoid these drawbacks, the proposal has been made to prepare cosmetic compositions in the form of an aqueous gel containing neither fat nor oil. However, to be of use in cosmetics, the gels must display the same qualities of hydration of the skin as the oil- or fat-based compositions used hitherto, and furthermore, on the one hand, they must have a silky and non-tacky feel and, on the other hand, they must be able to be taken out and spread easily. Moreover, the gels must be stable and compatible with the different additives generally used in cosmetic compositions, especially those which are electrolytes. Lastly, they must be transparent in order to have an attractive presentation.

A hydrating aqueous gel not containing oil, prepared using a poly(glyceryl methacrylate) as gelling agent and containing a polyol such as glycerol and polyethylene glycol, has been described in U.S. Pat. No. 4,863,725. However, this gel does not display all the desired cosmetic qualities; in particular, it does not have the desired silky feel.

SUMMARY OF THE INVENTION

According to the present invention, it has been found to be possible to obtain a cosmetic composition having the desired qualities by using as gelling agent a mixture of three polymers which are known separately for their gelling activity: a crosslinked acrylic acid copolymer, a copolymer of acrylic acid and vinyl monomer bearing nitrogen-containing functions, and a polyethylene glycol having a high molecular weight, the effects of these different polymers combining to give, unexpectedly, the desired result.

DESCRIPTION OF THE DRAWING

FIG. 1 shows curves demonstrating the effect of increasing quantities of aqueous NaCl to the gel obtained in Example 1, where the quantities Q of NaCl solution added are shown in ml as the abscissae and the viscosity is given in pascal seconds as ordinates.

DETAILED DESCRIPTION OF THE INVENTION

The subject of the present invention is a cosmetic composition in the form of an aqueous gel containing a gelling agent and an aqueous medium, characterized in that the gelling agent consists of a mixture of:

a) at least one at least partially neutralized, crosslinked acrylic acid polymer having a molecular weight of between 700,000 and 4,500,000 approximately, b) at least one at least partially neutralized copolymer of acrylic acid and vinyl monomer bearing amine, amidine and nitrile functions, and obtained by hydrolysis of polyacrylonitrile, having a molecular weight of between 100,000 and 200,000 approximately, and c) at least one polyethylene glycol having a molecular weight of between $10^5$ and $3\times10^7$ approximately.

This cosmetic composition is devoid of water-immiscible oils and fats; this expression is understood to mean that the composition contains at most 1% of water-immiscible oil or fat.

Preferably, the cosmetic composition contains:

from 0.1 to 1% of the polymer(s) defined in a), from 0.1 to 1% of the copolymer(s) defined in b), and from 0.01 to 1% of the polyethylene glycol(s) defined in c).

The crosslinked polyacrylic acids are gelling agents which are widely used for gelling aqueous solutions. They are designated CARBOMERS® in the CFTA dictionary, and are marketed under the name CARBOPOL® by the company Goodrich BF. When used alone, they produce tacky gels having an unpleasant feel. Furthermore, the gels obtained are sensitive to electrolytes and their viscosity decreases strongly in a saline medium.

The copolymers of acrylic acid and vinyl monomer containing amine, amidine and nitrile functions are designated "acrylic acid/acrylonitrogen" in the CFTA dictionary. They are, for example, marketed under the name HYPAN SA 100 H® by the company LIPO CHEMICALS Inc. When they are used alone, they give gels which break down readily, and which are consequently difficult to take out, for example from a jar, and difficult to spread on the skin.

The high molecular weight polyethylene glycols are polyethylene glycols of formula

$$H(OCH_2CH_2)_nOH$$

in which n is such that the molecular weight is above $10^5$ and below $3\times10^7$. Polyethylene glycol having a molecular weight in the region of 15 million is used more especially. It is possible to use, in particular, the polyethylene glycols marketed under the trade name POLYOX® by the company Union Carbide. These polyethylene glycols form thickened solutions which, when applied to the skin, give it a soft and silky feel. However, their thickening power is low and, alone, they do not enable a gel to be obtained. Furthermore, they are known to react with polyacrylic acids to form a precipitate.

According to the present invention, it has been found that, by combining the three polymers defined above, a gel is obtained which is less sensitive to electrolytes than crosslinked acrylic acid polymers, as will be shown below. Furthermore, surprisingly, although polyethylene glycols and polyacrylic acids are in contact, a precipitate is not formed and the gel consequently remains transparent. Lastly, the gel obtained according to the invention may be readily taken out and spread on the skin, and it is not tacky.

The crosslinked acrylic acid polymer defined under a) and the copolymer of acrylic acid and vinyl monomer defined under b) must be at least partially neutralized in order to be able to swell in the form of a gel. The neutralization is performed using any base, but it is preferable to use alkali metal hydroxides, alkanolamines, for example mono-, di- or triethanolamine, aminomethylpropanol, aminomethylpropanediol, tris(hydroxymethyl)aminomethane or N,N,N',N'-tetrakis(2-hydroxypropyl)ethylenediamine.

The composition according to the present invention can optionally contain another type of polymer as a gelling and hydrating agent, namely a poly(glyceryl acrylate) and/or poly(glyceryl methacrylate) advantageously having a viscosity of 400 to 5,000 pascal seconds as measured at 20° C. using a Brookfield RTV viscometer. According to the invention, it is possible, for example, to use the poly(glyceryl methacrylate) marketed under the name LUBRAJEL MS® by the company Guardian Inc., or the poly(glyceryl acrylate) marketed under the name HISPAGEL 100® by the company Hispano Chimica. The poly(glyceryl acrylate) and/or poly(glyceryl methacrylate) advantageously represent(s) 0.01 to 50% by weight of the composition.

The compositions according to the invention can advantageously contain at least one cosmetic active agent and/or at least one cosmetic formulation adjuvant. This active agent and/or this adjuvant can be any known cosmetic active agent or any known cosmetic adjuvant, on condition that it is soluble in water and compatible with the gel.

The water-soluble cosmetic active agent can be, for example, chosen from the group composed of humectant agents such as polyols, especially glycerol, propylene glycol, sorbitol and low molecular weight polyethylene glycols, skin care agents such as allantoin, panthenol and protein hydrolysates, astringents such as $C_1$–$C_4$ lower alcohols, sunscreen agents and anti-free-radical agents.

According to the present invention, the gel can also contain as active agent a quantity of a water-soluble oil such as oxyethylenated $C_6$–$C_{12}$ fatty acid glycerides, for instance the product marketed under the name SOFTIGEN 767® by the company Dynamit-Nobel, which is a mixture of oxyethylenated caprylic and captic glycerides containing 6 mol of ethylene oxide. These "water-soluble oils" are used in proportions not exceeding 10% by weight without impairing the transparency of the gel.

Depending on the active agent(s) used, the gel can have different applications. It can be, for example, a hydrating gel, a tonifying gel, an aftershave gel, an after-sun gel or a sun gel.

The water-soluble cosmetic formulation adjuvant can be, for example, chosen from the group composed of colorants, perfumes, preservatives and pH agents.

EXAMPLE 1

For the purposes of comparison, two aqueous gels were prepared: a gel $G_1$ according to the invention, containing three gelling polymers, and a gel $G_2$ not forming part of the invention.

| Starting materials | $G_1$ (in g) | $G_2$ (in g) |
| --- | --- | --- |
| Crosslinked polyacrylic acid marketed under the name CARBOPOL 940 ® by the company Goodrich BF | 0.25 | 0.16 |
| Copolymer of acrylic acid and vinyl monomer marketed under the name HYPAN SA 100 H ® by the company Lipo chemicals. | 0.25 | — |
| Polyethylene glycol marketed under the name "POLYOX COAGULANT ® company Union Carbide | 0.1 | — |
| N,N,N',N'-Tetrakis(2-hydroxypropyl)ethylenediamine marketed under the name QUADROL L ® by the company BASF | 0.3 | — |
| Triethanolamine | 0.25 | 0.16 |
| Distilled water qs | 100 | 100 |
| Viscosity (in pascal seconds) | 1.33 | 1.90 |
| pH | 6.6 ± 0.1 | 6.8 ± 0.1 |

Increasing quantities of 2% (by weight) aqueous NaCl solution were added to the gel obtained, and the viscosity was measured at 20° C. using a Contraves TV viscometer after each addition. The results are given on the curves in FIG. 1, attached, where the quantities Q of NaCl solution added are shown in ml as abscissae and the viscosity is given in pascal seconds as ordinates.

These curves show that the viscosity of the gel $G_2$ decreases much faster than that of the gel $G_1$ according to the invention.

EXAMPLE 2

A hydrating gel for the skin having the following formulation was prepared:

| | |
| --- | --- |
| Crosslinked polyacrylic acid marketed under the name CARBOPOL 940 ® by the company Goodrich BF | 0.28 g |
| Copolymer of acrylic acid and vinyl monomer marketed under the name "HYPAN SA 100 H ® by the company Lipo Chemicals | 0.15 g |
| Polyethylene glycol of molecular weight 15 million marketed under the name POLYOX ® by the company Union Carbide | 0.10 g |
| N,N,N',N'-Tetrakis(2-hydroxypropyl)ethylenediamine marketed under the name QUADROL L ® by the company BASF | 0.21 g |
| Triethanolamine | 0.17 g |
| Water qs | 100 g |

The gel obtained has a viscosity of 1.65 pascal seconds and a pH of 5.8±0.2. It is stable, transparent, has a silky feel and spreads easily.

EXAMPLE 3

A hydrating gel for the skin having the following formulation was prepared:

| | |
| --- | --- |
| Crosslinked polyacrylic acid marketed under the name CARBOPOL 940 ® by the company Goodrich BF | 0.28 g |
| Copolymer of acrylic acid and vinyl monomer marketed under the name HYPAN SA 100 H ® by the company "LIPO CHEMICALS" | 0.15 g |
| Polyethylene glycol of molecular weight 15 million marketed under the name POLYOX ® by the company Union Carbide | 0.10 g |
| Poly(glyceryl methacrylate) marketed under the name LUBRAJEL MS ® by the company Guardian Inc. | 10 g |
| N,N,N',N'-Tetrakis(2-hydroxypropyl)ethylenediamine marketed under the name QUADROL L ® by the company BASF | 0.21 g |
| Triethanolamine | 0.17 g |
| Water qs | 100 g |

The gel obtained has a viscosity of 1.7 pascal seconds and a pH of 5.9±0.2. It is stable, transparent, has a silky feel and spreads easily.

EXAMPLE 4

A hydrating gel for the skin containing hydrating agents and having the following formulation was prepared:

| | |
| --- | --- |
| Crosslinked polyacrylic acid marketed under the name CARBOPOL 940 ® by the company Goodrich BF | 0.28 g |
| Copolymer of acrylic acid and vinyl monomer marketed under the name HYPAN SA 100 H ® by the company Lipo Chemicals | 0.15 g |
| Polyethylene glycol of molecular weight | 0.10 g |

| | |
|---|---|
| 15 million marketed under the name POLYOX COAGULANT ® by the company Union Carbide | |
| Poly(glyceryl methacrylate) marketed under the name LUBRAJEL MS ® by the company Guardian Inc. | 20 g |
| N,N,N',N'-Tetrakis(2-hydroxypropyl)ethylenediamine marketed under the name QUADROL L ® by the company "BASF" | 0.21 g |
| Triethanolamine | 0.17 g |
| Propylene glycol | 3 g |
| Glycerol | 3 g |
| Polyethylene glycol containing 20 ethylene oxide units, marketed under the name CARBOWAX 1000 ® by the company Goodrich BF | 5 g |
| Preservatives qs | 5 g |
| Water qs | 100 g |

The gel obtained has a viscosity of 2.65 pascal seconds and a pH of 6.1±0.2. It is stable, transparent, has a silky feel and spreads easily.

We claim:

1. An aqueous gel cosmetic composition comprising an aqueous gel containing a gelling agent and an aqueous medium, said gelling agent consisting of (a) a partially neutralized, crosslinked acrylic acid polymer having a molecular weight of between 700,000 and 4,500,000 and present in an amount ranging from 0.1 to 1 percent by weight of said composition;

(b) a neutralized copolymer of acrylic acid and a vinyl monomer bearing amine, amidine and nitrile functions and obtained by hydrolysis of polyacrylonitrile, said copolymer having a molecular weight of between 100,000 and 200,000 and present in an amount ranging from 0.1 to 1 percent by weight of said composition; and (c) a polyethylene glycol having a molecular weight of between $10^5$ and $3 \times 10^7$ and present in an amount ranging from 0.01 to 1 percent by weight of said composition.

2. The cosmetic composition of claim 1 wherein said polyethylene glycol has a molecular weight of about 15 million.

3. The cosmetic composition of claim 1 which also contains a water-soluble cosmetic active agent, a water-soluble formulation adjuvant or a mixture thereof.

4. The cosmetic composition of claim 3 wherein said water-soluble cosmetic active agent is selected from the group consisting of a humectant agent, a skin care agent, an astringent, a sunscreen agent and an anti-free-radical agent.

5. The cosmetic composition of claim 3 wherein said water-soluble cosmetic active agent is a water-soluble oil present in an amount not exceeding 10 percent by weight of said composition.

6. The cosmetic composition of claim 3 wherein said water-soluble formulation adjuvant is selected from the group consisting of a colorant, a perfume, a preservative and a pH agent.

7. An aqueous gel cosmetic composition comprising an aqueous gel containing a gelling agent and an aqueous medium, said gelling agent consisting of (a) a partially neutralized, crosslinked acrylic acid polymer having a molecular weight of between 700,000 and 4,500,000 and present in an amount ranging from 0.1 to 1 percent by weight of said composition;

(b) a neutralized copolymer of acrylic acid and a vinyl monomer bearing amine, amidine and nitrile functions and obtained by hydrolysis of polyacrylonitrile, said copolymer having a molecular weight of between 100,000 and 200,000 and present in an amount ranging from 0.1 to 1 percent by weight of said composition;

(c) a polyethylene glycol having a molecular weight of between $10^5$ and $3 \times 10^7$ and present in an amount ranging from 0.01 to 1 percent by weight of said composition; and (d) an agent selected from the group consisting of a poly(glyceryl acrylate), a poly (glyceryl methacrylate) and a mixture thereof.

8. The cosmetic composition of claim 7 wherein said poly (glyceryl methacrylate) has a viscosity of 400 to 5,000 pascal seconds as measured at 20° C. using a Brookfield RFV viscometer.

* * * * *